(12) United States Patent
Tanaka

(10) Patent No.: US 6,930,705 B2
(45) Date of Patent: Aug. 16, 2005

(54) IMAGE SEARCH DEVICE

(75) Inventor: Chinari Tanaka, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 484 days.

(21) Appl. No.: 09/986,965

(22) Filed: Nov. 13, 2001

(65) Prior Publication Data

US 2002/0057341 A1 May 16, 2002

(30) Foreign Application Priority Data

Nov. 14, 2000 (JP) .................................... 2000-346440

(51) Int. Cl.$^7$ ............................................ H04N 13/00
(52) U.S. Cl. ........................... 348/45; 348/49; 600/173
(58) Field of Search ............................ 348/45, 42, 43, 348/44, 46–51, 72–78, 65–70, 143–147; 600/173, 118, 102, 168, 111; 700/65, 77, 66, 83, 250; 359/625, 626, 627, 628, 629, 638, 814, 823, 813, 833–836; H04N 13/00, 7/12; G02B 7/02

(56) References Cited

U.S. PATENT DOCUMENTS

| | | | | |
|---|---|---|---|---|
| 5,836,869 A | * | 11/1998 | Kudo et al. .................. | 600/173 |
| 5,871,439 A | * | 2/1999 | Takahashi et al. ........... | 600/118 |
| 6,402,685 B1 | * | 6/2002 | Igarashi ........................ | 600/111 |
| 6,490,490 B1 | * | 12/2002 | Uchikubo et al. ............. | 700/65 |
| 6,717,752 B2 | * | 4/2004 | Kanai ........................... | 359/814 |
| 2002/0057496 A1 | * | 5/2002 | Kanai ........................... | 359/625 |

FOREIGN PATENT DOCUMENTS

| | | |
|---|---|---|
| JP | 8-332169 | 12/1996 |
| JP | 10174673 | 6/1998 |

* cited by examiner

Primary Examiner—Tung Vo
(74) Attorney, Agent, or Firm—Greenblum & Bernstein, P.L.C.

(57) ABSTRACT

An endoscopic apparatus has an objective optical system arranged in a rigid endoscope for forming an image, a first image re-forming optical system for re-forming a part of the image once formed through the objective optical system on an image pickup surface of a first CCD camera and a second image re-forming optical system which re-forms an image once formed through an objective optical system on an image pickup surface of a second CCD camera. A second monitor displays the image picked up by the second CCD camera added with a rectangular frame indicating size and amplitude of the area corresponding to the image picked up by the first CCD camera.

9 Claims, 7 Drawing Sheets

IMAGE SEARCH DEVICE

BACKGROUND OF THE INVENTION

1. Field of the Invention

The present invention relates to an image search device for allowing the observer to look at any desired area of an image formed through an objective optical system.

2. Description of the Related Art

An endoscopic apparatus of a certain type designed for medical applications is installed with an image search device that displays an enlarged view of a part of a wide-angle image of an object formed through an objective optical system arranged at a distal end of the endoscope and allows the observer to search a target area to be observed within the wide-angle image by shifting the enlarged view within the wide-angle image. With an endoscopic apparatus incorporated with such an image search device, an operator can observe the image of a wide area inside a body cavity of a patient displayed on a screen of one monitor and, at the same time, an enlarged image of a particular area displayed on a screen of other monitor.

However, conventional image search devices are not provided with means for indicating the area in the image of the wide area displayed on the screen of the former monitor, which corresponds to the enlarged image displayed on the screen of the latter monitor. Therefore, the operator is forced to compare frequently the two images on the two display screens in order to identify the limited area in the image of the wide area corresponding to the enlarged image which is burdensome for the operator, and which prolongs the operation so long as to gruel the operator and to endanger the life of the patient.

SUMMARY OF THE INVENTION

One object of the present invention is to provide an image search device by which a target area in an image formed through its objective optical system and displayed on a screen of one monitor can be enlarged and displayed on a screen of other monitor and by which the area is indicated in the image displayed on the screen of the former monitor.

According to the invention, the above object is achieved by providing an image search device which has a first image pickup optical system, a first image pickup device for picking up an image of a predetermined visual field formed through the first image pickup optical system to output a first image signal representing the picked up image, a second image pickup optical system including at least one lens for forming an image of at least a part of the predetermined visual field, a second image pickup device for picking up the image formed through the second image pickup optical system to output a second image signal representing the picked up image, a shift unit for shifting an area to be picked up by the second image pickup device through the second image pickup optical system within the predetermined visual field by shifting an optical axis of the lense in said second image pickup optical system relative to the second image pickup device, an image synthesizing unit for adding an image signal representing a mark showing the area corresponding to the image picked up by the second image pickup device to the first image signal based on an amount of the relative shift of said optical axis to the second image pickup device, a first display unit for displaying the image represented by the first image signal performed with the synthetic processing by the image synthesizing unit, and a second display unit for displaying the image represented by the second image signal.

With the above described arrangement, as the optical axis of the lens in the second image pickup optical system and the second image pickup device are shifted relative to each other by the shift unit, the area to be picked up by the second image pickup device is shifted within the visual field. Thus, the image searched from the imaging area picked up by the first image pickup device is displayed on the second display unit. At this time, the image synthesizing unit adds an image signal representing a mark showing the area corresponding to the image picked up by the second image pickup device to said first image signal, based on the amount of the relative shift of the optical axis. As a result, the image of the visual field superimposed with the mark indicating the area corresponding to the image picked up by the second image pickup device is displayed on the screen of the first display unit. Thus, the operator can immediately identify the area in the image displayed on the screen of the first display unit, which corresponds to the image displayed on the screen of the second display unit.

The image search device according to the invention may be incorporated into a rigid or fiber endoscope or a surveillance camera.

The shift unit may shift an optical axis of the lens in the second image pickup optical system while the second image pickup device is secured in position. Alternatively, the second image pickup device may be moved in a plane perpendicular to the optical axis, while the optical axis is secured in position. In the former case, the lenses themselves may be shifted or an optical system to deflect or shift the optical axis may be used. An image erecting prism or reflex mirrors having a function same as the image erecting prism may be used for such a device. More specifically, a Pechan prism having a roof, an Abbe prism having a roof, a first type Porro prism, a second type Porro prism or a set of plurality of mirrors arranged at respective positions equivalent to the reflection surfaces of one of those prisms may be used. In short, an image reflecting optical system having four or more reflection surfaces may be used as the shift unit.

The first and second image pickup optical systems may be independent optical systems having respective optical axes running in parallel with each other or may be such that they share a lens on their front side. Each of the first and second image pickup optical systems may include an objective optical system and an image re-forming optical system. In this case, same objective optical system may be shared between the first and second image pickup optical systems.

The image re-forming optical system may include a variator to change magnifying power of the whole image re-forming optical system by moving along its optical axis. In this case, the magnifying power of the whole image re-forming optical system changes as the variator moves, so that the area, within the image picked up by the first image pickup device, corresponding to the image picked up by the second image pickup device may be enlarged or contracted. Therefore, preferably the image synthesizing unit may changes the size of the area shown by the mark according to the position of the variator.

The present disclosure relates to subject matter contained in Japanese Patent Application No. 2000-346440 (filed on November 14, 2000), which is expressly incorporated herein by reference in its entirety.

The invention will be described below in detail with reference to accompanying drawings, in which.

DESCRIPTION OF THE PREFERRED EMBODIMENTS

Now, the present invention will be described by referring to the accompanying drawings that illustrate preferred embodiments of the invention.

First Embodiment

Figure 1:
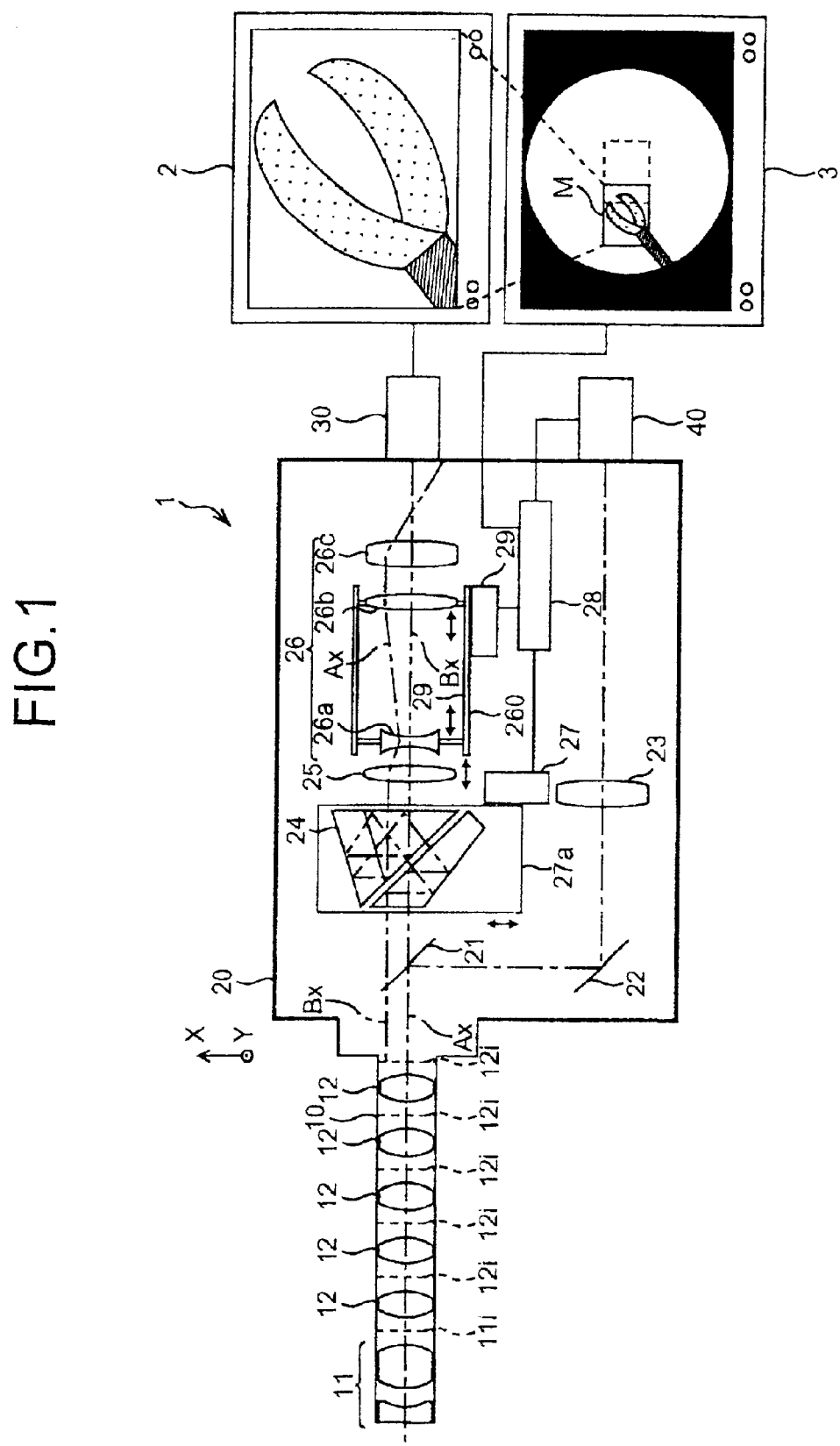
FIG. 1 is a schematic illustration of an optical arrangement and an internal arrangement of an endoscopic apparatus as a first embodiment of the invention.

A first embodiment of the image search device according to the invention is incorporated into an endoscopic apparatus 1. Referring to FIG. 1, the endoscopic apparatus 1 has a rigid endoscope 10 to be inserted into a body cavity through a trocar pierced up to the abdominal wall of the patient, an image separating device 20 to which the rigid endoscope 10 is connected, first and second CCD cameras 40, 30 functioning as image pickup devices for picking up respective images relayed through the optical system built in the image separating device 20, and first and second monitors 3, 2 respectively connected to the first and second CCD cameras 40, 30.

Each of the first and second CCD cameras 40, 30 is adapted to pick up a moving image by means of an ordinary solid imaging device (CCD), converts the object light entering its image pickup surface into a video signal, process the obtained video signal appropriately and then output the video signal to each of first and second monitors 3, 2.

The rigid endoscope 10 has inside an objective optical system for forming an image of inside of the body cavity and relaying it, a light guide for guiding illumination light from a light source (not shown) to the distal end of the endoscope 10 in order to illuminate the body cavity, which are incorporated in a linear tube. The objective optical system has an objective lens group 11 and a plurality of relay lenses 12. The objective lens group 11 is a retro-focus type objective lens which can form an image of a wide view angle (e. g., more than 120°). The image of the body cavity is formed on the image plane 11i through the objective lens group 11. Then, the image formed on the image plane 11i is sequentially refocused on the image planes 12i of the respective relay lenses 12 until it is relayed to the image plane 12i of the rearmost relay lens 12.

The image separating device 20 contains inside a half mirror 21, a reflection mirror 22, a Pechan prism 24, a focusing lens 25, a second image re-forming optical system including first through third lens groups 26a through 26c and a first image re-forming optical system 23 comprising a single positive lens. The half mirror 21 functioning as a separating optical member is arranged on the light path of the object light coming from the objective optical system in the rigid endoscope 10 to reflect a part of the object light and to transmit the remaining part thereof. The reflection mirror 22 is arranged on the light path of the object light reflected by the half mirror 21. Thus, the optical axis Ax of the objective optical system is bent by the half mirror 21 and then bent again by the reflection mirror 22 to run along the optical axis of the first image re-forming optical system 23 and therefore perpendicularly strikes the center of the imaging area of the first CCD camera 40 connected to the image separating device 20.

With the above described arrangement, the object light reflected by the half mirror 21 is reflected again by the reflection mirror 22 and transmitted through the first image re-forming optical system 23 to enter the image pickup surface of the first CCD camera 40. The first CCD camera 40 picks up the image formed through the objective optical system (comprising an objective lens group 11 and a plurality of relay lenses 12) arranged in the rigid endoscope 10 and relayed by the first image re-forming optical system 23 and outputs a video signal (that is, a first image signal) representing the picked up image.

Figure 2:
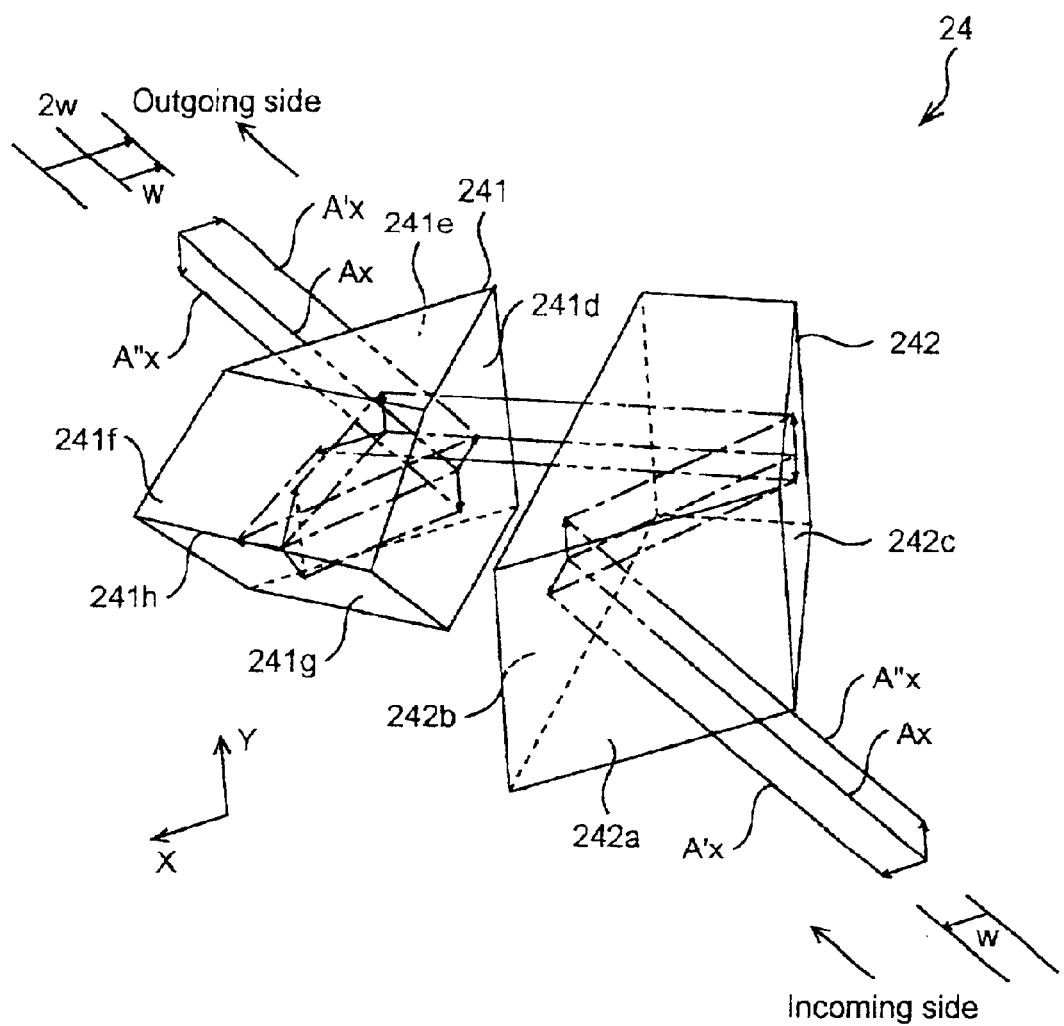
FIG. 2 is an enlarged perspective view of a Pechan prism that is used in the first embodiment.

On the other hand, the Pechan prism 24 functioning as an optical axis shifting member and an image erecting optical system is held on the light path of the object light transmitted through the half mirror 21 in such a way that it can be shifted in the X-direction that is perpendicular to the optical axis Ax of the objective optical system and also in the Y-direction that is perpendicular to both the X-direction and the optical axis Ax. FIG. 2 is a perspective view of the Pechan prism that is used in the first embodiment. As seen from FIGS. 1 and 2, the Pechan prism 24 consists of a roof prism 241 having a shape equivalent to a form where a side surface of a triangular prism is replaced by the roof consisting of surfaces 241f and 241g (with the ridge line 241h of the roof parallel with the bottom surface of the triangular prism) and an auxiliary prism 242 that is a quadratic prism having a side surface 242b parallel with a side surface of the roof prism 241. The optical axis Ax of the objective optical system transmitted through the half mirror 21 enters perpendicularly into the auxiliary prism 242 of the Pechan prism 24 through its side surface 242a and bent twice by the inner surfaces of the two side surfaces 242b, 242c of the auxiliary prism 242 located adjacent to the side surface 242a and passes perpendicularly through the side surface 242b of the auxiliary prism 242 and the side surface 241d of the roof prism 241. Thereafter, the optical axis Ax is bent sequentially by the inner surfaces of the side surface 241e, the roof 241f, 241g and the side surface 241d of the roof prism 241 and then exit from the roof prism 241 perpendicularly through the side surface 241e (in a direction parallel to the optical axis Ax before entering the auxiliary prism 242). Note that the extension of the optical axis Ax before entering the Pechan prism 24 runs through the center of the imaging area of the second CCD camera 30 connected to the image separating device 20. The position of the Pechan prism 24 at which the optical axis Ax before entering the Pechan prism 24 is coaxial with the optical axis Ax after exiting from the Pechan prism 24 is referred to as initial position of the Pechan prism 24 hereinafter.

The focusing lens 25 is arranged coaxial with the optical axis Ax of the objective optical system after exiting from the Pechan prism 24 in the initial position. The focusing lens 25 is movable along its optical axis. The focusing lens 25 is moved by a focusing actuator (not shown) typically being a DC servo motor or a stepping motor.

The first through third lens groups 26a through 26c of the second image re-forming optical system 26 are arranged between the focusing lens 25 and the second CCD camera 30 also coaxial with the optical axis Ax of the objective optical system after exiting from the Pechan prism 24 in the initial position. The third lens group 26c is fixed, while the first and second lens groups 26a, 26b functioning as a variator are held by a zoom lens barrel 260, movably along their optical axes. As an unillustrated can ring composing the zoom lens barrel 260 rotates about the optical axis of the lens groups 26a, 26b, each of the lens groups 26a, 26b having a can follower engaged with a can groove formed inside the can ring moves along the optical axis. Therefore, the second image re-forming optical system 26 can appropriately change its magnification. The can ring is rotated by a zooming actuator typically being a DC servo motor or a stepping motor.

With the above described arrangement, the object light transmitted through the half mirror 21 is then sequentially transmitted through the Pechan prism 24, the focusing lens 25 and the second image re-forming optical system 26 before it enters the image pickup surface of the second CCD camera 30. More specifically, the Pechan prism 24 inverts and reverses the image formed through the objective optical system (comprising the objective lens group 11 and the plurality of relay lenses 12) arranged in the rigid endoscope 10, and the second image re-forming optical system 26 enlarges a part of the image formed through the objective optical system with a predetermined magnification to re-form the image on the image pickup surface of the second CCD camera 30. Then, the second CCD camera 30 picks up the image formed through the first image re-forming optical system 26 and outputs a video signal (that is, a second image signal) representing the picked up image. Thereafter, the image is displayed on the screen of the second monitor 2 according to the video signal.

The Pechan prism 24 is movable within the XY-plane as X- and Y-stages 27a are driven by a moving mechanism 27. More specifically, the moving mechanism 27 functioning as a shift unit includes a drive actuator typically being a DC servo motor or a stepping motor and a gear system for transmitting the drive force of the drive actuator to each of the X- and Y-stages so that the X- and Y-stages may be driven independently. The moving mechanism 27 is connected to an operation unit (not shown) including a joy-stick that can be tilted along a cross. As the operator operates the joy-stick, a signal representing the degree and direction of the tilted joy-stick is transmitted to the moving mechanism 27. Upon receiving the signal, the moving mechanism 27 drives the X- and Y-stages 27a according to the degree and direction of the tilted joy stick indicated by the signal so that the Pechan prism 24 is moved within the XY-plane. The operation unit (not shown) may alternatively include a track ball to be rotated by the operator to output a signal representing the extent and direction of rotation of the track ball. Still alternatively, the operation unit may include a lever for the X-direction and a lever for the Y-direction to output a signal representing the extent and direction of each of the tilted levers.

As the Pechan prism 24 is moved within the XY-plane from the initial position, the optical axis Ax of the objective optical system after exiting from the Pechan prism 24 is shifted relative to the optical axis of the second image re-forming optical system 26. FIG. 2 schematically illustrates how the optical axis Ax of the objective optical system is shifted relative to the optical axis of the second image re-forming optical system 26 through the Pechan prism 24. As shown in FIG. 2, when the optical axis Ax before entering the Pechan prism 24 having been at its initial position shifts positively in the X-direction (leftward in FIG. 2) by distance w relative to the side surface 24a, the optical axis Ax after exiting from the Pechan prism 24 is moved negatively in the X-direction also by distance w relative to the side surface 24e. That corresponds to the case where the Pechan prism 24 moves negatively in the X-direction (rightward in FIG. 2) by distance w relative to the stationary optical axis Ax of the objective optical system before entering the Pechan prism 24. Therefore, in that case, the optical axis Ax' of the objective optical system after exiting from the Pechan prism 24 is shifted negatively in the X-direction by distance 2w relative to the optical axis Ax' of the objective optical system before entering the Pechan prism 24. Inversely, when the Pechan prism 24 is moved positively in the X-direction, the optical axis Ax of the objective optical system after exiting from the Pechan prism 24 is shifted positively in the X-direction by a distance twice as long as the distance of movement of the Pechan prism 24. Similarly, when the Pechan prism 24 is moved in the Y-direction (vertical direction in FIG. 2), the optical axis Ax" of the objective optical system after exiting from the Pechan prism 24 is shifted relative to the optical axis Ax" before entering the Pechan prism 24 in the direction of movement of the Pechan prism 24 by a distance twice as long as the distance of movement of the Pechan prism 24.

Figure 3:
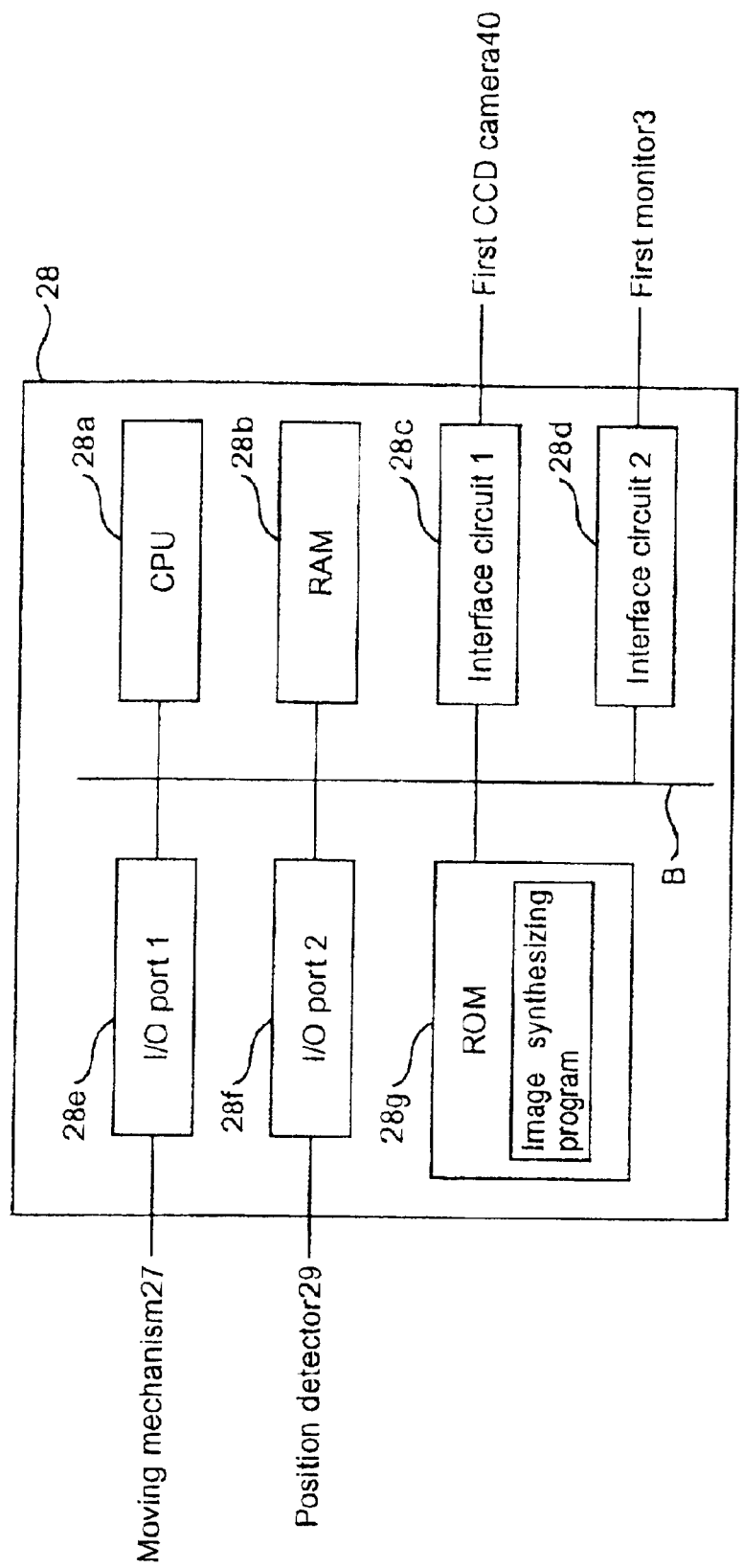
FIG. 3 is a block diagram schematically showing internal circuit in the image synthesizing unit.

Thus, as the Pechan prism 24 is shifted within the XY-plane, the optical axis Ax" of the objective optical system after exiting from the Pechan prism 24 is shifted from a line coaxial with the optical axis Bx of the second image re-forming optical system 26. FIG. 3 illustrates this situation. If the Pechan prism 24 is at its initial position where the optical axis Ax of the objective optical system after exiting from the Pechan prism 24 is coaxial with the optical axis Bx of the second image re-forming optical system 26, a light beam traveling on the optical axis Ax of the objective optical system travels on the optical axis Bx of the second image re-forming optical system 26 and enters the center of the image pickup surface of the second CCD camera 30. However, as the Pechan prism 24 is moved within the XY-plane as shown in FIG. 1, the optical axis Ax after exiting from the Pechan prism 24 is shifted from the optical axis Bx of the second image re-forming optical system 26. Thus, the light beam traveling on the optical axis Ax of the objective optical system is shifted from the optical axis Bx of the second image re-forming optical system 26 and enters the image pickup surface of the second CCD camera 30 at a position shifted from the center thereof, so that the area of the image picked up by the second CCD camera 30 shifts. Therefore, the Pechan prism 24, the X- and Y-stages 27a and the moving mechanism 27 correspond to the shift unit.

The objective optical system of the rigid endoscope 10 shows a large curvature field, because the objective optical lens group 11 has a wide visual field and the image formed through the objective lens group 11 is relayed through the relay lenses 12. Therefore, as the image formed through the objective optical system is moved in the X- and Y-directions relative to the visual field of the second image re-forming optical system 26, the image will also be moved toward and away on the optical axis Bx from a plane conjugate to the image pickup surface of the second CCD camera 30 with respect to the second image re-forming optical system 26, which may cause defocus on the image picked up by the second CCD camera 30. However, this problem can be solved by using a focusing control circuit (not shown) to drive the focusing actuator in synchronism with the moving mechanism 27 according to the distance by which the optical axis Ax of the objective optical system is shifted from the optical axis Bx of the second image re-forming optical system 26 so that plane conjugate to the image pickup surface of the second CCD camera 30 with respect to the second image re-forming optical system 26 and the image plane of the objective optical system may intersect on the optical axis Bx.

The image separating device 20 further contains an image synthesizing unit 28 for synthetically combining the image signal (first image signal) output from the first CCD camera 40 with the image signal representing a frame as the mark indicating an area, in the image picked up by the first CCD camera 40, corresponding to an image picked up by the second CCD camera 30, and a position detector 29 for detecting the position of the first lens group 26a and that of the second lens group 26b of the second image re-forming optical system 26 to notify the image synthesizing unit 28 thereof.

The position detector 29 detects the positions of the first and second lens groups 26a, 26b that are moved along the optical axis of the second image re-forming optical system 26 by a zooming actuator (not shown). More specifically, the position detector 29 detects a rotary position of the cam ring of the zoom lens barrel 260 holding the first and second lens groups 26a, 26b by means of an encoder and notifies the image synthesizing unit 28 of the rotary position of the cam ring as positional information on the first and second lens groups 26a, 26b (that is, a zooming positional information).

FIG. 3 is a block diagram schematically showing internal circuit of the image synthesizing unit 28. As shown in FIG. 3, the image synthesizing unit 28 has a CPU 28a, a RAM 28b, a first interface circuit 28c, a second interface circuit 28d, a first I/O port 28e, a second I/O port 28f, and a ROM 28g, which are connected to each other through a bus B.

The CPU 28a controls the components 28b through 28g. The RAM 28b caches various programs read by the CPU 28a and is used for processing by the CPU 28a. The first interface circuit 28c is adapted to receive image signals from the first CCD camera 40. The second interface circuit 28d is adapted to transmit image signals to the first monitor 3. The first I/O port 28e is adapted to receive information on the amount of movement of the X-stage and that of the Y-stage (that is, the amount of shift of the optical axis Ax) from the moving mechanism 27 according to an instruction issued by the CPU 28a. The second I/O port 28f is adapted to receive the zooming positional information from the position detector 29 according to an instruction issued by the CPU 28a.

Figure 4:
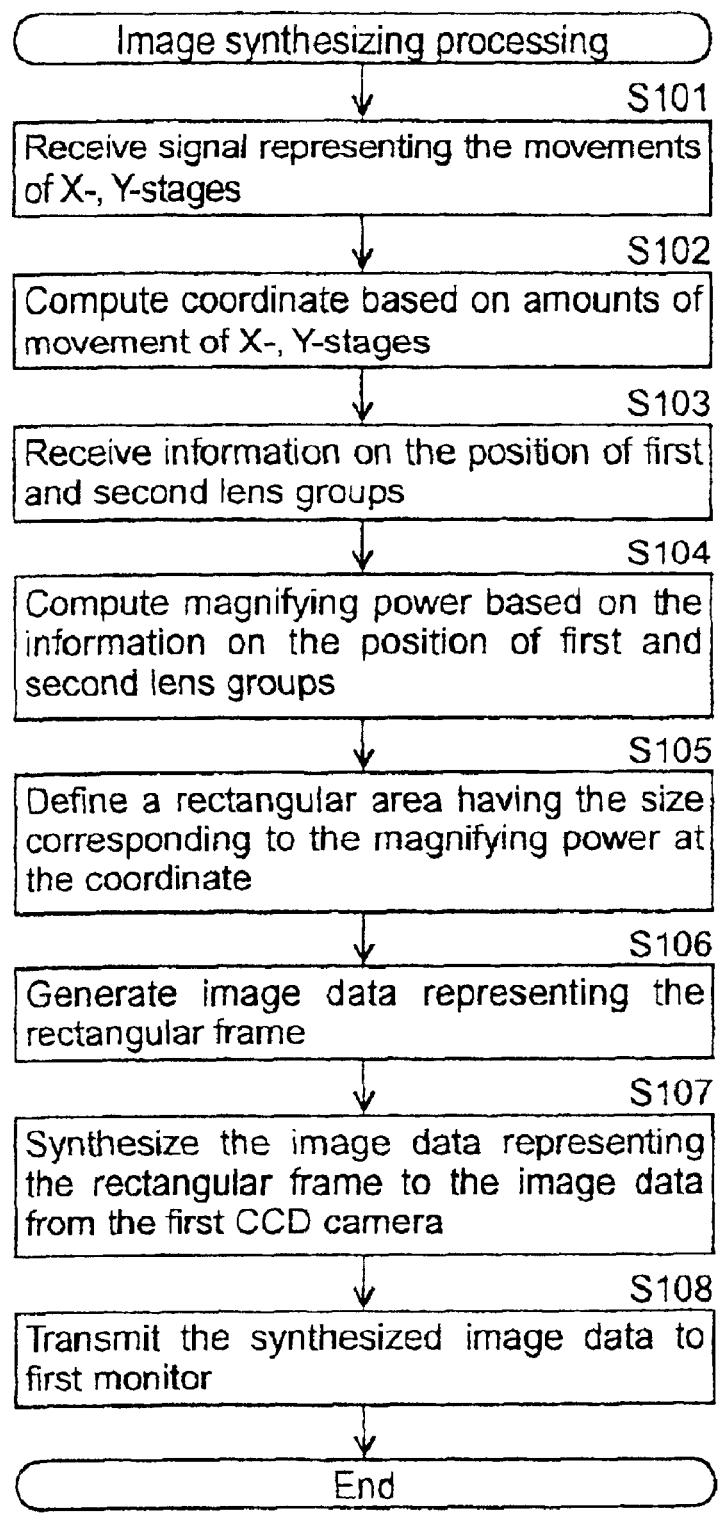
FIG. 4 is a flowchart showing an image synthesizing processing executed by the image synthesizing unit.

The ROM 28g is a storage medium storing various data and programs. The programs stored in the ROM 28g include an image synthesizing program that causes the CPU 28a to perform an image synthesizing processing as shown in the flow chart of FIG. 4. The image synthesizing processing starts when the CPU 28a receives an image signal from the first CCD camera 40 through the first interface circuit 28c.

After starting, in the first Step S101, the CPU 28a receives the information on the amount of movement of the X-stage and that of the Y-stage from the moving mechanism 27 through the first I/O port 28e.

Then, in Step S102, the CPU 28a updates the information on the position of each of the stages stored in the RAM 28b on the basis of the information received on S101, and computes coordinate of a position corresponding to the optical axis Bx of the second image re-forming optical system 26 in a coordinate system defined to indicate the area of the image displayed on the first monitor 3 on the bases of the information stored in the RAM 28b. This can be done because the position of the optical axis Bx of the second image re-forming optical system 26 depends on the position of the Pechan prism 24 that is moved by the X- and Y-stages 27a in the XY-plane.

In Step S103 the CPU 28a receives the zooming positional information from the position detector 29 through the second I/O pot 28f.

In Step S104, the CPU 28a computes the magnifying power of the second image re-forming optical system 26 based on the zooming positional information received in Step S103.

Then, in Step S105, the CPU 28a defines a rectangular area in the above coordinate system that has a size corresponding to the magnifying power computed in Step S104 (=the size of the above coordinate system×the magnifying power of the first image re-forming optical system 23/the magnifying power of the second image re-forming operation system 26) and same aspect ratio as the coordinate system and is centered at the coordinate computed in Step S102.

Figure 5:
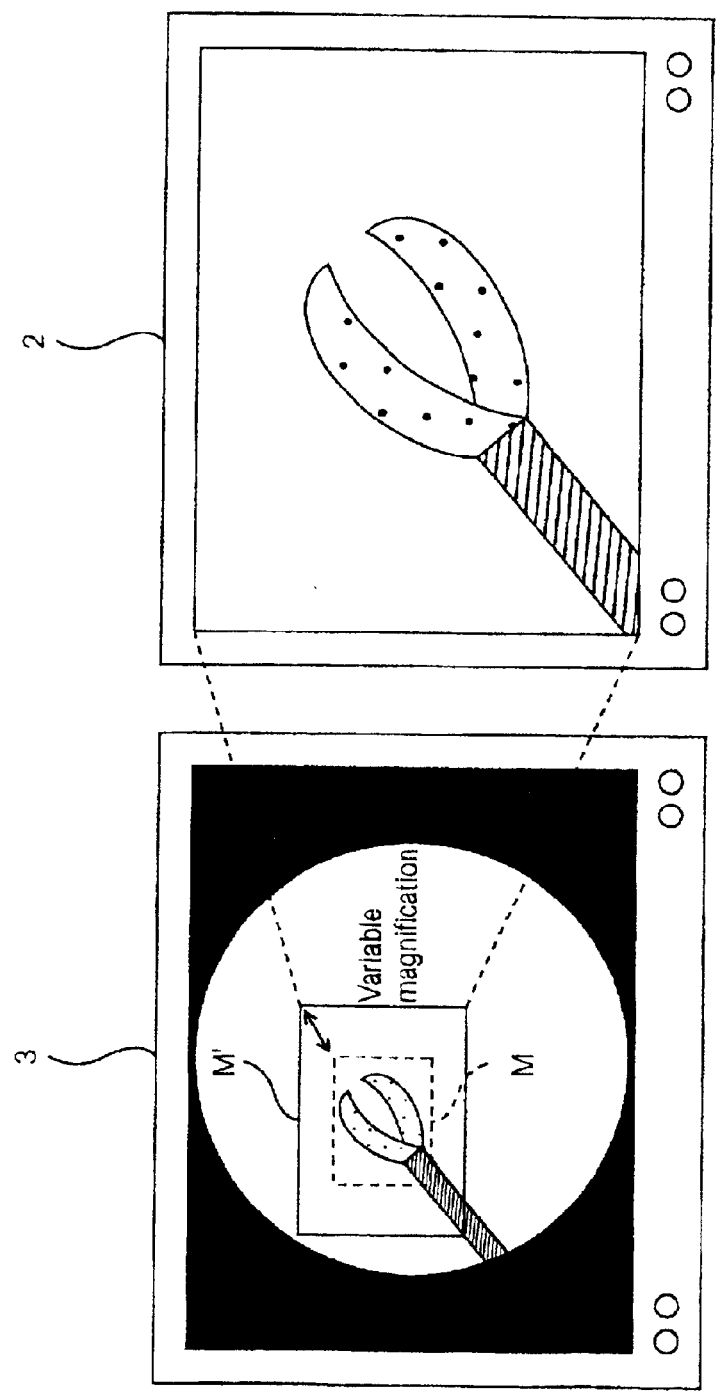
FIG. 5 shows an example of images respectively displayed on the first and second monitors.

Thereafter, in Step S106, the CPU 28a generates an image signal for displaying a rectangular frame (M in FIG. 1) surrounding the rectangular area defined in Step Sl05. It will be appreciated that the rectangular area in said coordinate system corresponds to the shape and the position of area in the image displayed on the screen of the first monitor 3 according to the image signal from the first CCD camera 40, which corresponds to the image displayed on the screen of the second monitor 2 according to the image signal from the second CCD camera 30. Therefore, the size of the rectangular area and that of the rectangular frame M depends on the focal length (magnifying power) of the second image re-forming optical system 26 as shown in FIG. 5.

Then, in Step S107, the CPU 28a synthetically adds the image signal for displaying the rectangular frame M generated in Step S106 to the image signal received from the first CCD camera 40 through the first interface circuit 28c.

In Step S108, the CPU 28a outputs the image signal which is synthesized with the image signal for displaying the rectangular frame M in Step S107 to the first monitor 3 through the second interface circuit 28d and ends this image synthesizing processing. As the processing of Step S108 is carried out, the first monitor 3 displays an image in which the rectangular frame M indicating the area corresponding to the image picked up by the second CCD camera 30 and displayed on the screen of the second monitor 2 is superimposed on the image formed through the objective optical system of the rigid endoscope 10 and picked up by the first CCD camera 40.

The above described image synthesizing processing is carried out each time the CPU 28a receives an image signal from the first CCD camera 40 through the first interface circuit 28c. As the image synthesizing processing is repeatedly executed, the rectangular frame M in the image displayed on the screen of the first monitor 3 moves smoothly in synchronism with the movement of the Pechan prism 24 and also is enlarged or contracted in synchronism with the movement of the first and second lens groups 26a, 26b.

As described above, with the endoscopic apparatus 1 according to the first embodiment, when the image formed through the objective optical system in the rigid endoscope 10 is displayed on the screen of the first monitor 3 and a target area which is searched from the image by shifting the image relative to the visual field of the second image re-forming optical system 26, the area to be picked up by the second CCD camera 30 is indicated in the image displayed on the screen of the first monitor 3 by a rectangular frame M. Therefore, the operator can clearly identify the area in the image displayed on the screen of the first monitor 3, which corresponds to the enlarged image displayed on the screen of the second monitor 2.

Second Embodiment

Figure 6:
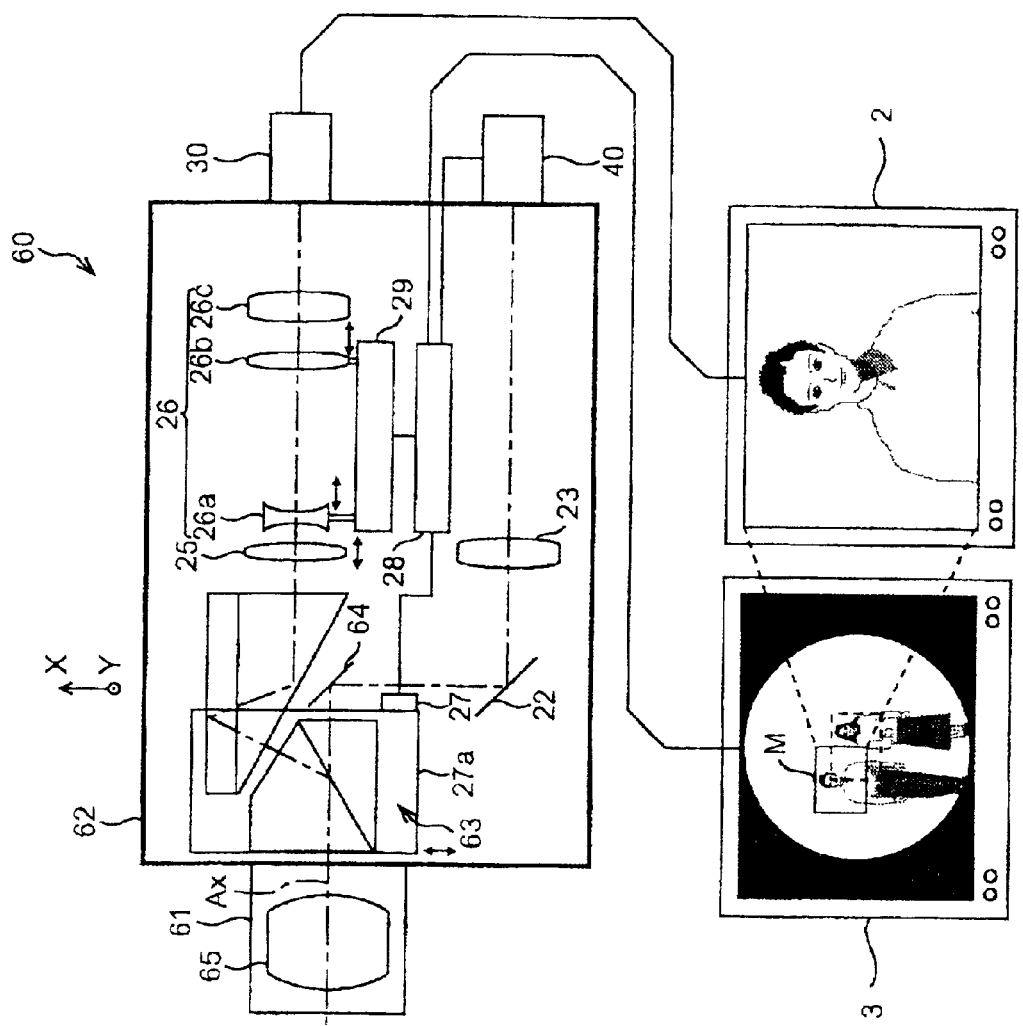
FIG. 6 is a schematic illustration of an optical arrangement and an internal arrangement of a surveillance camera as a second embodiment of the invention.

A second embodiment of the image search device according to the invention is incorporated into a surveillance camera 60. Referring to FIG. 6, the surveillance camera 60 has a main body 62 that corresponds to the image separating device 20 in the first embodiment, a lens barrel 61 mounted in front of the main body 62 and first and second CCD cameras 40, 30 functioning as image pickup devices mounted to the rear of the main body 62. As clearly shown in FIGS. 1 and 6, the arrangement of the surveillance camera 60 of the third embodiment is substantially similar to that of the endoscopic apparatus 1 of the first embodiment. Therefore, the components similar to those of the endoscopic apparatus 1 of the first embodiment are respectively denoted by the same reference number and their explanations are omitted.

The lens barrel 61 contains an objective optical system 65 having a wide view angle of about 120°. The image of the space to be monitored is formed through the objective optical system 65.

The main body 62 contains an Abbe prism 63 having a roof, a reflection mirror 64, another reflection mirror 22, a focusing lens 25, a second image re-forming optical system 26 and a first image re-forming optical system 23.

Figure 7:
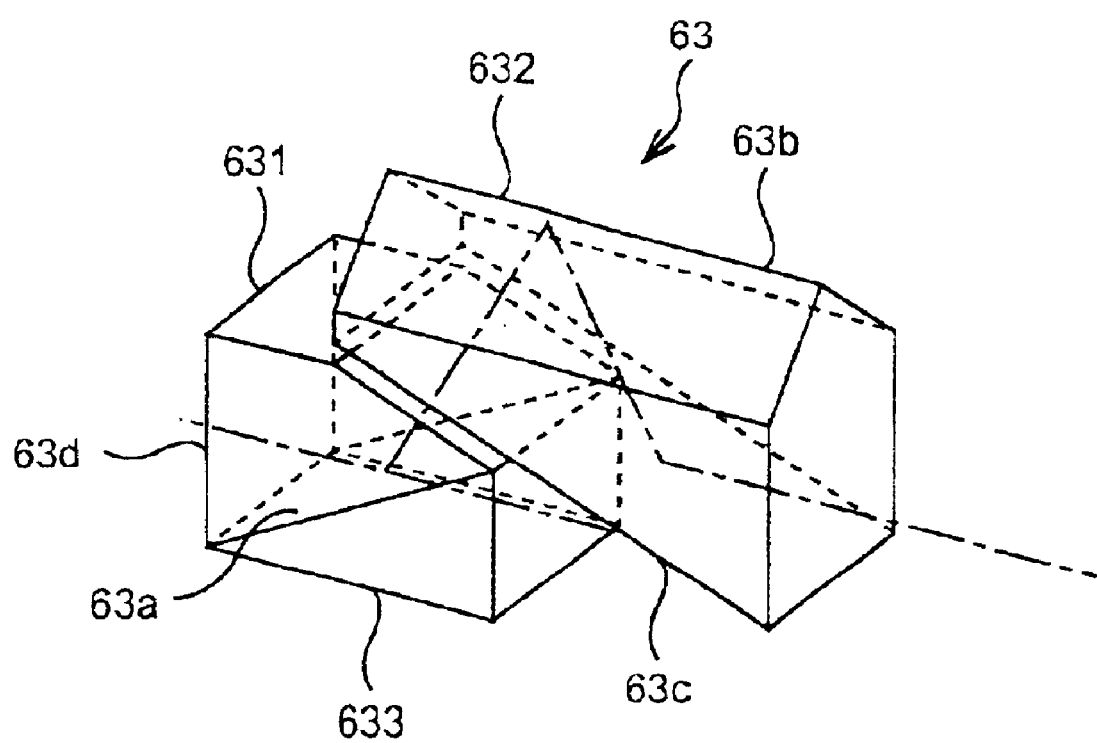
FIG. 7 is an enlarged perspective view of an Abbe prism that is used in the second embodiment.

The Abbe prism 63 functioning as an optical axis shifting member and an image erecting optical system is held on the light path of the object light in such a way that it can be shifted in the X-direction that is perpendicular to the optical axis Ax of the objective optical system 65 and also in the Y-direction that is perpendicular to both the X-direction and the optical axis Ax. FIG. 7 is an enlarged perspective view of the Abbe prism 63. As seen from FIGS. 6 and 7, the Abbe prism 63 basically has a first reflection surface 63a adapted to bend the optical axis Ax of the objective optical system 65 entering it perpendicularly through the incident surface 63d by an angle of 120°, a second reflection surface 63b formed as a roof having a ridge parallel with the optical axis Ax passing through the incident surface 63d and adapted to further bend the optical axis Ax that has been bent by the first reflection surface 63a, and a third reflection surface 63c adapted to further bend the optical axis Ax that has been bent by the second reflection surface 63b by an angle of 120° to the direction parallel with the optical axis Ax passing through the incident surface 63d. Note that the Abbe prism 63 is separated into a first prism 631 having the first reflection surface 63a and a second prism 632 having the second and third reflection surfaces 63b, 63c for the convenience of manufacturing, along the third reflection surface 63c. The first reflection surface 63a of the first prism 631 is a partial reflection surface and bonded to a triangular prism 633 to form a beam splitter.

In this embodiment, the optical axis of the focusing lens 25 and the second image re-forming optical system 26 is offset in the X-direction (vertical direction in FIG. 6) from the optical axis Ax of the objective optical system 65. The position of the Abbe prism 63 where the optical axis Ax of the objective optical system 65 that has been bent by the Abbe prism 63 coincides with the optical axis of the focusing lens 25 and the second image re-forming optical system 26 is referred to as an initial position hereinafter.

With the above described arrangement, the object light transmitted through the objective optical system 65 is then sequentially transmitted through the Abbe prism 63, the focusing lens 25, and the second image re-forming optical system 26, and enters the image pickup surface of the second CCD camera 30. At this time, the Abbe prism 63 inverts and reverses the image formed through the objective optical system 65 and the second image re-forming optical system 26 enlarges an area of the image with a predetermined magnification and to re-form it on the image pickup surface of the second CCD camera 30. Then, the image re-formed by the second image re-forming optical system 26 is picked up by the second CCD camera 30 and displayed on the screen of the second monitor 2 that is connected to the second CCD camera 30.

The Abbe prism 63 is moved as a whole within the XY-plane as the X- and Y-stages 27a are driven by a moving mechanism 27. As the Abbe prism 63 is moved from the initial position in X- and/or Y-directions, the optical axis Ax of the objective optical system 65 after exiting from the Abbe prism 63 is shifted from the optical axis of the second image re-forming optical system 26 in the direction of movement of the Abbe prism 63 by a distance twice as long as the distance of movement of the Abbe prism 63. FIG. 6 schematically illustrates a case where an area decentered from the center of the image displayed on the screen of the first monitor 3 is enlarged with a predetermined magnification and displayed on the screen of the second monitor 2 through the Abbe prism 63 which is displaced from its initial position. In FIG. 6, the broken lines in the image on the screen of the first monitor 3 indicates area picked up by the second CCD camera 30 when the Abbe prism 63 is at its initial position.

The reflection mirror 64 is arranged on the optical path of the object light transmitted through the first reflection surface 63a of the Abbe prism 63 in order to bend the optical axis Ax of the objective optical system 65 separated by the first reflection surface 63a by 90°. Another reflection mirror 22 is arranged on the optical path of the object light reflected by the reflection mirror 64. Thus, the optical axis Ax of the objective optical system 65 is further bent by the reflection mirror 22, coaxially passes through the first image re-forming optical system 23 and perpendicularly enters the center of the imaging area of the first CCD camera.

With the above described arrangement, the object light that has passed through the first reflection surface 63a is sequentially reflected by the two reflection mirrors 64, 22, passes through the first image re-forming optical system 23 and enters the image pickup surface of the first CCD camera 40. The first CCD camera 40 picks up the image formed by the objective optical system 65 and relayed through the first image re-forming optical system 23. The picked up image is then displayed on the screen of the first monitor 3 connected to the first CCD camera 40.

As the moving mechanism 27, the position detector 29 and the image synthesizing unit 28 function as explained in the first embodiment, the monitor 3 displays an image in which the rectangular frame M indicating the area corresponding to the image displayed on the screen of the second monitor 2 is superimposed on the image of the space to be displayed on the screen of the first monitor 3. Therefore, an observer can clearly identify the area in the image displayed on the screen of the first monitor 3 which corresponds to the enlarged image displayed on the screen of the second monitor 2.

As described above in detail, according to the invention, it is possible to search and detect a target area to be observed in the image formed on the imaging plane through the objective optical system and displayed on the screen of the first monitor and to display an image of the area on the screen of the second monitor. At the same time, the area displayed on the screen of the second monitor is indicated by a mark on the image displayed on the screen of the first monitor. Thus, the observer can clearly identify the position and the area corresponding to the image displayed on the screen of the second monitor in the wide-angle image displayed on the screen of the first monitor by seeing the mark in the wide-angle image.

What is claimed is:

1. An image search device comprising:
    a first image pickup optical system;
    a first image pickup device which picks up an image of a predetermined visual field formed through said first image pickup optical system to output a first image signal representing the picked up image;
    a second image pickup optical system including at least one lens which forms an image of at least a part of the predetermined visual field;
    a second image pickup device which picks up the image formed through said second image pickup optical system to output a second image signal representing the picked up image;
    a shift unit which shifts an area to be picked up by said second image pickup device through said second image pickup optical system within the predetermined visual field by shifting an optical axis of the lens in said second image pickup optical system relative to said second image pickup device, said shift unit comprising an optical axis shifting member which shifts the optical axis by moving in a plane perpendicular to the optical axis, and a moving unit which moves the optical axis shifting member, said optical axis shifting member comprising an image erecting optical system comprising at least four reflection surfaces;

an image synthesizing unit which adds, to the first image signal, an image signal representing a mark showing the area corresponding to the image picked up by said second image pickup device based on an amount of the relative shift of said optical axis with respect to said second image pickup device;

a first display unit which displays the image represented by said first image signal processed by said image synthesizing unit; and a second display unit which displays the image represented by said second image signal.

2. The image search device according to claim 1, wherein said first image pickup optical system and said second image pickup optical system share an objective optical system including the lens whose optical axis is shifted by said shift unit relative to said second image pickup device, and a separating optical member which separates object light that passed through the objective optical system; and said second image pickup optical system has an image re-forming optical system arranged at a rear of said separating optical member to relay at least a part of an image formed through said objective optical system.

3. The image search device according to claim 2, wherein said image re-forming optical system includes a variator that changes a magnifying power of the whole image re-forming optical system by moving along an optical axis of the variator; and said image synthesizing unit computes an amplitude of the area corresponding to the image picked up by said second image pickup device in the image picked up by said first image pickup device based on a position of said variator and generates an image signal representing the mark showing the area having the computed amplitude.

4. The image search device according to claim 2, wherein said objective optical system is incorporated in an endoscope.

5. The image search device according to claim 2, wherein said objective optical system is incorporated in a surveillance camera.

6. An image search device comprising:

a first image pickup optical system;

a first image pickup device which picks up an image of a predetermined visual field formed through said first image pickup optical system to output a first image signal representing the picked up image;

a second image pickup optical system including at least one lens which forms an image of at least a part of the predetermined visual field;

a second image pickup device which picks up the image formed through said second image pickup optical system to output a second image signal representing the picked up image;

a shift unit which shifts an area to be picked up by said second image pickup device through said second image pickup optical system within the predetermined visual field, by shifting an optical axis of the lens in said second image pickup optical system relative to said second image pickup device;

an image synthesizing unit which adds, to the first image signal, an image signal representing a mark showing the area corresponding to the image picked up by said second image pickup device, based on an amount of the relative shift of said optical axis with respect to said second image pickup device;

a first display unit which displays the image represented by said first image signal processed by said image synthesizing unit; and a second display unit which displays the image represented by said second image signal, wherein, said first image pickup optical system and said second image pickup optical system share an objective optical system including the lens whose optical axis is shifted by said shift unit relative to said second image pickup device, and a separating optical member which separates object light that passed through the objective optical system; and said second image pickup optical system has an image re-forming optical system positioned at a rear of said separating optical member to relay at least a part of an image formed through said objective optical system, and wherein said image re-forming optical system includes a variator that changes a magnifying power of the whole image re-forming optical system by moving along its optical axis; and said image synthesizing unit computes an amplitude of the area corresponding to the image picked up by said second image pickup device in the image picked up by said first image pickup device based on a position of said variator and generates an image signal representing the mark showing the area having the computed amplitude.

7. The image search device according to claim 6, wherein said shift unit comprises an optical axis shifting member which shifts the optical axis by moving in a plane perpendicular to the optical axis, and a moving unit which moves the optical axis shifting member.

8. The image search device according to claim 6, wherein said objective optical system is incorporated in an endoscope.

9. The image search device according to claim 6, wherein said objective optical system is incorporated in a surveillance camera.

* * * * *